(12) United States Patent
Bae et al.

(10) Patent No.: US 7,786,345 B2
(45) Date of Patent: Aug. 31, 2010

(54) TRANSGENIC PLANTS EXPRESSING CELLULASE FOR AUTOHYDROLYSIS OF CELLULOSE COMPONENTS AND METHODS FOR PRODUCTION OF SOLUBLE SUGAR

(75) Inventors: Hyeun-Jong Bae, Gwangju (KR); Inhwan Hwang, Pohang-si (KR); Serge Laberge, aire Saint-Foy (CA); Ginette Turcotte, Toronto (CA)

(73) Assignee: Postech Foundation, Gyeongsangbuk-Do (KR)

( * ) Notice: Subject to any disclaimer, the term of this patent is extended or adjusted under 35 U.S.C. 154(b) by 318 days.

(21) Appl. No.: 11/572,869

(22) PCT Filed: Jul. 30, 2005

(86) PCT No.: PCT/KR2005/002494
§ 371 (c)(1),
(2), (4) Date: Mar. 5, 2007

(87) PCT Pub. No.: WO2006/011779
PCT Pub. Date: Feb. 2, 2006

(65) Prior Publication Data
US 2007/0226840 A1    Sep. 27, 2007

(30) Foreign Application Priority Data
Jul. 30, 2004    (KR)    ..................... 10-2004-0060618

(51) Int. Cl.
C12N 15/82    (2006.01)
C12N 15/11    (2006.01)
C12N 15/00    (2006.01)
A01H 3/00    (2006.01)

(52) U.S. Cl. .................. 800/278; 800/295; 800/288; 435/320.1; 435/469; 536/23.1; 536/23.7

(58) Field of Classification Search .................. None
See application file for complete search history.

(56) References Cited

U.S. PATENT DOCUMENTS

| | | | |
|---|---|---|---|
| 6,365,390 B1 * | 4/2002 | Blum et al. ................. | 435/197 |
| 6,365,799 B1 * | 4/2002 | Waldron ..................... | 800/278 |
| 6,429,359 B1 * | 8/2002 | Lamppa ..................... | 800/288 |
| 2002/0138878 A1 * | 9/2002 | Sticklen et al. ............. | 800/288 |
| 2003/0054535 A1 * | 3/2003 | Himmel et al. ............. | 435/209 |
| 2003/0109011 A1 * | 6/2003 | Hood et al. ................. | 435/105 |
| 2004/0005674 A1 * | 1/2004 | Duck et al. ................. | 435/105 |

OTHER PUBLICATIONS

Karita et al 1997 Journal of Fermentation and Bionengineering 84:354-357, provided in Applicant's IDS.*
Jin et al 2003 Plant Molecular Biology 51:493-507, reference provided by Applicant.*
Shuichi Karita, et al., Purification of the Puminococcus Albus Endoglucanase IV . . . , Journal of Fermentation and Bioengineering, vol. 84, No. 4, pp. 354-357, 1997.
Hyeun-Jong Bae, et al., CEL6B of Thermobifidus Fusca and a CEL5-CBM6 of Ruminococcus . . . , FEMS Microbiology Letters, vol. 233, pp. 325-331, 2004.
Ziyu Dai, et al., Expression of Acidothermus Cellulyticus Endoglucanase . . . , Transgenic Research, vol. 9, pp. 43-54, 2000.
Tetsu Kawazu, et al., Expression of a Bacterial Endoglucanase Gene in Tobacco . . . , Journal of Bioscience and Bioengineering, vol. 88, No. 4, pp. 421-425, 1999.
Jin, et al., "Expression and import of an active cellulase from a thermophilic bacterium into the chloroplast both in vitro and in vivo", Plant Molecular Biology, 2003, 51(4):493-507.
Ziegelhoffer, et al., "Dramatic effects of truncation and sub-cellular targeting on the accumulation of recombinant microbial cellulase in tobacco", Molecular Breeding, 2001, 8(2):147-158.

* cited by examiner

*Primary Examiner*—Anne Marie Grunberg
*Assistant Examiner*—Brent Page
(74) *Attorney, Agent, or Firm*—Lucas & Mercanti, LLP

(57) ABSTRACT

The present invention relates to transgenic plants for producing cellulose by a mechanism of autohydrolysis and a method producing soluble sugars using them, more particularly to transgenic plants transformed with recombinant cDNA coding cellulase, cellulose binding domain and chloroplast targeting peptide and a method producing soluble sugars using them. Transgenic plants and a method producing soluble sugars using them would be a highly cost-effective system for the production of soluble sugars on a large scale.

4 Claims, 5 Drawing Sheets

(1)           (2)           (3)

SEQUENCE LISTING

```
<160> NUMBER OF SEQ ID NOS: 1

<210> SEQ ID NO 1
<211> LENGTH: 1357
<212> TYPE: DNA
<213> ORGANISM: Artificial Sequence
<220> FEATURE:
<223> OTHER INFORMATION: RbcS(tp): Cel5: CBM6

<400> SEQUENCE: 1
atgttggata aacttaaagt aataaatgga aaactgacag ccggtgagaa accagtaaga      60
cttttcgggt tatcaactca cggtatagcc tggtatccgg aatatatttg tgaagaatca     120
ttcaatgccc taaaaaaaga ctggcgtaca aactgtataa ggatagcaat gtacacagac     180 gaattcgag ggtactgcaa ggacggcaac aaacagcatc tgaaagagct gatcgagaaa     240
ggcgttgtta ttgcagaaaa actggatatg tatgtaatag tagactggca cgttctgtgt     300
```

```
gatcaggatc cgatgaaata tattgatgaa gctgaagagt ttttcagtga tatgtcaaag      360
aggttcgcca ataaaacaaa cgttatatac gagatatgta acgaacctaa ctgcagcggc      420
acatgggata aaataacaga atatgcagac aggataatcc cgataatccg cagtaactcc      480
cccgatgcac ttattgtcac aggaacatca acgtggtcgc aggacataca ctgtgcgctt      540
gaaaagccgc tgaaatggga caatgttatg tactctctgc atttctatgc tgctacacac      600
aagggtacac tgcgcagcag actggaacga tgtattgaag ccgggcttcc ggtttttatc      660
aatgaattca atctgtgtga agctagcggt aagggcgata tcgatataga tgaagcaaat      720
gcatggtatg aggtaataga cagactcggg ctgagctgca taagctggtg cctttcaaac      780
agtggagata cctgcggcgt ttttacccaa aattgtacaa agctttcagg ctggacggat      840
gaagatataa aaacatcggg caaaataata aaaggctggt ttgaggcatt tgcagatgag      900
gagaatacaa atgaacaatg ttttcgaagt tcaccagtgc ctgcacctgg tgataacaca      960
agagacgcat attctatcat tcaggccgag gattatgaca gcagttatgg tcccaacctt     1020
caaatcttta gcttaccagg tggtggcagc gccattggct atattgaaaa tggttattcc     1080
actacctata aaaatattga ttttggtgac ggcgcaacgt ccgtaacagc aagagtagct     1140
acccagaatg ctactaccat tcaggtaaga ttgggaagtc catcgggtac attacttgga     1200
acaatttacg tggggtccac aggaagcttt gatacttata gggatgtatc cgctaccatt     1260
agtaatactg cgggtgtaaa agatattgtt cttgtattct caggtcctgt taatgttgac     1320
tggtttgtat tctcaaaatc aggaacttaa ggagctc                              1357
```

TRANSGENIC PLANTS EXPRESSING CELLULASE FOR AUTOHYDROLYSIS OF CELLULOSE COMPONENTS AND METHODS FOR PRODUCTION OF SOLUBLE SUGAR

TECHNICAL FIELD

The present invention relates to transgenic plants expressing cellulase for autohydrolysis of cellulose components and a method for production of soluble sugar using the same, more particularly, transgenic plants produced by transfecting plants with recombinant cDNA encoding cellulose, cellulose binding domain and chloroplast targeting peptide and a method for production of soluble sugar by autohydrolysis of cellulose of the transgenic plants.

BACKGROUND ART

Plant biomass is the most abundant, natural and renewable resource on earth. Cellulose is the major constituent of plant cell walls and is a commercially important raw material that can be converted into useful products with appropriate methodologies (Hon DN Cellulose: a random walk along its historical path, In Cellulose. J. C. Roberts (ed.), Chapman & Hall, 1-25, 1994). One such application is the production of fermentable sugars from cellulose for the production of biofuel ethanol. Because of the potentially high importance of this process, cellulose-degrading enzymes have received a great deal of attention (Beltrane P L et al., Bioresource Technol. 39: 165-171, 1992). To date, the conversion of plant cellulose into fermentable sugars is accomplished with commercial enzymes produced by large-scale fermentation. However, the cost of producing these enzymes remains a significant barrier to the widespread utilization of this process (Cowan D, Tibtech. 14: 177-178, 1996; Ho N W et al., Adv. Biochem. Eng. Biotechnol. 65: 163-192, 1999). Thus, various approaches have been taken to produce cellulose-degrading enzymes on a large scale and at low cost (Goddijin O J M and Pen J, Trends biotechnol. 13: 3790-3870, 1995; Gidding G et al., Nature Biotech. 18: 1151-1155, 2000). *Trichoderma reesei* has been a target strain for the production of cellulase, and *Bacillus* and *Aspergillus* microorganisms have been a target for the production of xylanase. But, the concentration and activity of such enzyme is not enough to be used in industry. High production costs are also a problem, resulted from a high priced purified medium containing expensive materials such as lactose as a substrate for the production of the enzyme.

Genetically engineered transgenic plants are one of the most economical systems for large scale production of recombinant proteins for industrial and medical uses, because a large quantity of enzymes can be produced with minimal input. In efforts to lower the production costs of cellulases (Jensen L G et al., Proc. Natl. Acad. Sci. 93: 3487-3491, 1996; Kawazu T et al., J. Ferment. Bioeng. 82: 205-209, 1996; Nuutila A M et al., Plant Mol. Biol. 41: 777-783, 1999; Ziegelhoffer T et al., Mol. Breed. 5: 309-318, 1999; Dai Z et al., Transgenic Res. 9: 43-54, 2000), the cellulase gene has been expressed in transgenic plants, but the expression levels obtained have been low. The purification of recombinant cellulases expressed in plants is also an expensive step, which contributes greatly to the cost of production of fermentable sugars from cellulose.

Thus, the present inventors produced transgenic plants in which a recombinant gene containing cellulase gene, cellulose binding domain gene and chloroplast targeting gene was inserted. And the present inventors completed this invention by confirming that the conversion of cellulose into fermentable sugar is possible in transgenic plants themselves by autohydrolysis using cellulose localized in chloroplasts, and the production cost is also reduced by simplifying the production line of soluble sugar from cellulose.

DISCLOSURE

Technical Problem

It is an object of the present invention to provide transgenic plants produced by inserting recombinant cDNA encoding cellulose, cellulose binding domain and chloroplast targeting peptide in plants and a method for production of soluble fermentable sugars from cellulose with low costs by autohydrolysis of the plants.

Technical Solution

In order to achieve the above object, the present invention provides transgenic plants transfected with cDNA encoding cellulose, cellulose binding domain and chloroplast targeting peptide.

The present invention also provides a method for the production of soluble sugar from cellulose in transgenic plants having cellulose autohydrolysis activity.

Hereinafter, the present invention is described in detail.

The present invention provides an expression vector for plant transformation which is expressed in a plant and contains recombinant cDNA encoding cellulase, cellulose binding domain and chloroplast targeting peptide.

The expression vector above can be designed to express endoglucanase, exoglucanase, or endo- and exoglucanase simultaneously, and the cellulose gene above is a gene originated from non-plants, preferably from microorganisms, and more preferably from *Ruminococcus albus* (Ce15 cellulase gene). The ce15 cellulase is a kind of cellulase having very strong activity against soluble cellulose substrate.

Fusing the cellulose binding domain to the C-terminus of Cel5 increases its affinity for cellulose in the cell wall, resulting in the increase of the activity of cellulase. In a preferred embodiment of the present invention, CBM6 gene originated from Xylanase A of *Clostridium stercorarium* was used.

In addition, a sequence involved in the targeting of a specific cell can be fused to Ce15 N-terminus. The sequence for targeting above might be a solution for toxicity of a heterologous protein expressed in transgenic plants. In a preferred embodiment of the present invention, N-terminal transit peptide (RbcS(tp)) of rubisco small subunit was fused to N-terminal of Ce15:CBM6 for the migration of cellulase expressed in transgenic plants to the inside of chloroplast.

The recombinant cDNA encoding cellulase, cellulose binding domain and chloroplast targeting peptide, represented by SEQ. ID. No 1, can be fused to a promoter activated in a plant, and can be fused to an alfalfa rubisco small subunit promoter RbcSK-1A, in a preferred embodiment of the present invention (Khoudi et al., Gene 197:343-351, 1997).

The present invention provides an expression vector for plant transformation which contains the above recombinant gene, more particularly, the invention provides a pHB-Cel5:CBM6 vector designed to express RbcS(tp):Cel5:CBM6 under the control of RbcSK-1A promoter by using pCambia2300.

The present invention provides transgenic plants having autohydrolysis activity of cellulose.

The present invention provides a novel transgenic plant generated by transfecting tobacco cells with pHB-Cel5:CBM6 expression vector containing recombinant cDNA represented by SEQ. ID. No 1.

To generate the transgenic plant, *Agrobacterium tumefaciens* LBA-4404 was transfected with the recombinant expression vector pHB-Cel5:CBM6, resulting in a transformant to be used as a mediator for the generation of a transferred plant expressing RbcS(tp):Cel5:CBM6, and the present inventors deposited the transformant at Korean Collection for Type Cultures (KCTC) of Korea Research Institute of Bioscience and Biotechnology on Jun. 28, 2004 (Accession No: KCTC 10834BP).

In an embodiment of transgenic plants expressing RbcS (tp):Cel5:CBM6 of the present invention, a recombinant gene was inserted into tobacco leaf cells by leaf disc transformation using *Agrobacterium tumefaciens* LBA4404, and the cells were cultured under plant growth conditions, resulting in a transgenic tobacco (Harsch et al., Science 227:1229-1231, 1985).

The present invention also provides a method for the production of a transgenic plant expressing cellulase for autohydrolysis.

The method for the production of a transgenic plant of the present invention comprises the steps of i) constructing a plant expression vector harboring a gene encoding RbcS(tp):Cel5:CBM6; ii) transfecting plant cells using a recombinant microorganism transfected with the plant expression vector of i) to express RbcS(tp):Cel5:CBM6 in the plant cells; and iii) culturing the plant cells of ii) under plant growth conditions.

In a preferred embodiment of the present invention, *Agrobacterium tumefaciens* LBA4404 (Accession No: KCTC 10834BP) was used as a transgenic recombinant microorganism of the above ii), and tobacco or Dicotyledons were used as a plant of the invention.

The present inventors observed phenotypes of grown-up transgenic plants to investigate whether or not the growth of a transgenic tobacco plant having autohydrolysis activity of cellulose was affected by the toxicity of introduced cellulose gene. As a result, the transgenic plants in which only Cel5:CBM6 gene was introduced in cytoplasm had a severe growth defect. However, the transgenic plants harboring recombinant gene RbcS(tp):Cel5:CBM6 containing cellulase, cellulose binding domain and chloroplast targeting gene sequences did not show any visible morphological changes (see FIG. 1B). The above results indicate that cellulase expressed in a transgenic plant did not stayed in cytoplasm but targeted to the chloroplast by chloroplast targeting gene sequence.

The transgenic plant of the present invention has autohydrolysis activity against cellulose of its own cell wall by the accumulation of cellulase in chloroplasts.

Particularly, when the leaf or stem tissue homogenate of transgenic tobacco plants was incubated under optimal conditions, the chloroplast-localized Cel5:CBM6 was highly effective in the degradation of cellulose in the cell wall without any additional steps, resulting in the conversion of 12% of the total insoluble cellulose into soluble sugars. When a recombinant protein that was expressed and purified from *E. coli* and composed of cellulase and cellulose binding domain was externally added, autohydrolysis activity therein was nearly the same as that in the transgenic plant of the invention (see FIG. 3).

The present invention also provides a method for production of soluble sugar from cellulose using a transgenic plant having cellulose autohydrolysis activity.

The method for production of soluble sugar using a transgenic plant of the present invention includes following steps; i) obtaining homogenate from leaves or stems of a transgenic plant; ii) incubating the homogenate of the above step i) to induce autohydrolysis of cellulose; and iii) separating and purifying autohydrolyzed soluble sugars.

Application of the method of the present invention reduces the cost of production by simplifying the production lines since the expression and purification processes for externally added recombinant cellulases are not necessary.

In the soluble sugar production method of the present invention, 40% of the total insoluble cellulose was released as soluble sugars by the addition of externally expressed and purified exoglucanase to the homogenate of the step i).

The above results indicate that the introduction of a recombinant gene designed for co-expression of an exoglucanase together with endoglucanase enhances the production of soluble sugars on a large scale without the need for additional step of treating externally prepared exoglucanase.

Pink line: before autohydrolysis

Black line: after autohydrolysis

BEST MODE

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Generation of Transgenic Plants Having Autohydrolysis Activity of Cellulose

<1-1> Construction of Expression Vectors for Plant Transformation

The present inventors constructed expression vectors harboring cellulase, cellulose binding domain and chloroplast targeting peptide genes to generate transgenic tobacco plants containing cellulase gene being able to hydrolyze cellulose of their own cell walls.

Particularly, Cel5 gene of *Ruminococcus albus* having strong activity against soluble cellulose substrate and CBM6, which is a cellulose binding domain gene known to enhance affinity to cellulose of cell wall, were fused, resulting in a recombinant gene Cel5:CBM6. The recombinant gene Cel5:CBM6 was amplified by polymerase chain reaction (PCR) using pRA11 and pCsCBD as templates, followed by insertion into T/A cloning vector (Karita et al., Ferment. Bioeng. 76:439-444, 1993; Karita et al., Ferment. Bioeng. 84:354-357, 1997).

pRA11 and pCsCBD were provided by Dr. Karita (Department of Bioscience, Mie University, Tsu 514, Japan). PCR was performed with 30 cycles of 94° C./15 seconds, 55° C./30 seconds, and 72° C./1 minute.

Figure 1:
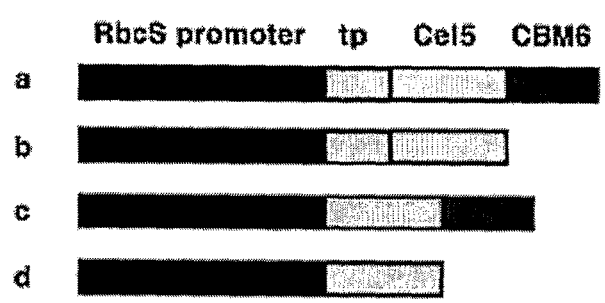
FIG. 1A is a schematic diagram showing the recombinant DNA construct inserted into a transgenic plant of the present invention,
  tp: Chloroplast targeting gene
  Cel5: Endo-beta-1,4,-glucanase (cellulase)
  CBM: Cellulose binding module
FIG. 1B is a set of photographs showing the growth of transgenic plants transfected with basic vector (a), recombinant gene RbcS(tp):Cel5:CBM6 of the present invention (b), and recombinant gene Cel5:CBM without chloroplast targeting gene (c)
Figure 1:
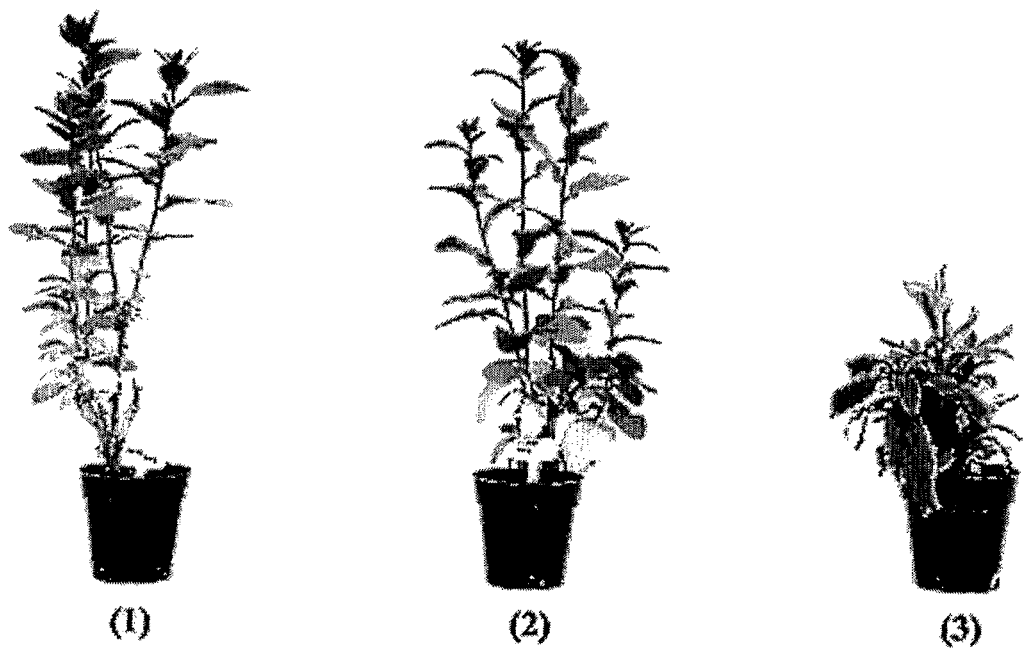

DNA fragments containing Cel5 and Cel5:CBM6 genes were separated from the vector above after treating restriction enzyme thereto, followed by subcloning into pKitmus54. DNA fragments containing the *R. albus* cellulase gene (eglV) and its modified version (eglV-CBDII) were amplified by polymerase chain reaction (PCR) using plasmids pRA11 and pCsCBD2 (Karita S. et al., J. Ferment. Bioeng. 76, 439-444, 1993; Karita et al., J. Ferment. Bioeng. 84, 354-357, 1997) as templates. The amplified PCR fragments were cloned in the T/A cloning vector. The recombinant plasmid containing eglv was digested with SacI/XbaI, and the recombinant plasmid containing eglV-CBDII was digested with SacI/SphI. The resultant inserts were conjugated respectively to pKitmus 54 and pKitmus 61. The first construct (pKitmus-54) was fused in 1.828 kb size alfalfa Rubisco small subunit (RbcSK-1A) promoter region and 3' noncoding sequence during translation. The promoter region included 5' noncoding leader sequence and the first 9 amino acids of chloroplast targeting peptide. The second construct (pKitmus-61) also contained RbcKS-1A promoter and 3' noncoding sequence, but it did not include transit peptide (FIG. 1). The recombinant plasmids pKitmus-54 and pKitmus-61 were digested with SalI and SmaI and the resultant inserts eglV and eglV-CBDII containing promoter and 3' noncoding region were subcloned into the corresponding region of a plant transformation vector pCambia2300 (Cambia, Canberra, Australia). The recombinant vectors were named pHB54 and pHB61.

The resulting construct pHB54 is a recombinant vector giving translational fusion proteins with the N-terminal transit peptide from the rubisco small subunit, RbcS(tp), under the control of the rubisco small subunit promoter from alfalfa.

Finally, Cel5, Cel5:CBM6, RbcS(tp):Cel5 and RbcS(tp):Cel5:CBM6 were subcloned with their promoters into a plant transformation vector pCambia2300 (Cambia, Canberra, Australia), resulting in the construction of recombinant vectors pHB54(F), pHB54, pHB61(F) and pHB61 (FIG. 1A).

<1-2> Generation of Transgenic Tobacco

The present inventors generated transgenic tobacco plants by inserting the expression vectors constructed in the above Example <1-1> into *Agrobacterium tumefaciens* LBA-4404 using leaf disc transformation method (Horsch R. B. et al., Science 227: 1229-1231, 1985).

First, *Agrobacterium tumefaciens* LBA-4404 was transfected with the above recombinant expression vector by electroporation. And the transformed cells were distributed on LB agar plate containing 10 μg/ml of kanamycin and 5 μg/ml of tetracycline, which was then cultured at 28° C. for 2 days. Transformants were selected, which were deposited at Korean Collection for Type Cultures (KCTC) of Korea Research Institute of Bioscience and Biotechnology on Jun. 28, 2004 (Accession No: KCTC 10834BP).

The leaf discs of *Nicotiana bentamiana* were inoculated with the above *Agrobacterium tumefaciens* LBA-4404, followed by culture for 2 days to insert cellulase gene included in the recombinant vector into chromosome of tobacco leaf cells. The transformed leaf discs were transferred onto MS selection medium (supplemented with 0.5 ml/l bovine albumin, Murashige-Skoog salt, 3% sucrose, 100 mg/l kanamycin, 250 mg/l pseudopen and 0.8% agar) to induce callus formation. The generated callus was grown up for one month and then the revived stem was transferred to a seedbed containing vermiculite, perlite and peat moss by the equal amount, followed by further culture in a 26° C. incubator under the 16 hour day-length condition to grow a transgenic tobacco plant.

The present inventors investigated phenotype of the grown up transgenic tobacco plant to examine the growth of the transgenic plant. As a result, transgenic tobacco plants expressing Cel5:CBM6 in cytoplasm had a severe growth defect. On the contrary, transgenic plants expressing RbcS(tp):Cel5;CBM6 did not show any visible morphological alterations (see FIG. 1B).

The above results indicate that a recombinant protein expressed in a transgenic tobacco plant was targeted to chloroplasts by chloroplast targeting peptide RbcS(tp), preventing toxicity possibly caused by a recombinant protein in a transgenic plant.

EXAMPLE 2

Expression of Cellulase in a Transgenic Tobacco Plant and Confirmation of the Cellulase Activity <2-1> Investigation on Expression of Recombinant Cellulase in a Transgenic Tobacco Plant In order to confirm whether or not a recombinant cellulase could be expressed normally in a transgenic tobacco plant, total RNA and total protein extracts were obtained from fifty independent lines of transgenic plants expressing RbcS(tp):Cel5:CBM6, and then Northern blot and Western blot were performed.

As a result, the expression of the inserted cellulase gene was observed in chloroplasts or in cytosol even though the expression level varied amongst the transgenic lines. Tb54(F)-14 and Tb54-8, expressing RbcS(tp):Cel5;CBM6 and RbcS(tp):Cel5 recombinant proteins respectively, were selected to quantify the cellulase protein in chloroplasts. The amount of cellulase protein in the chloroplasts of Tb54(F)-14 was 0.38% of the total soluble protein, and in Tb54-8 was 0.22% of the total soluble protein.

<2-2> Localization of a Recombinant Cellulase in a Transgenic Tobacco Plant

Immunolocalization was performed by using anti-cellulase (anti-Cel5) antibody to localize a recombinant cellulase in a transgenic tobacco plant.

Leaf samples were fixed with 4% formaldehyde in 100 mM cacodylate buffer (pH7.2) for 24 hours, washed in the same buffer, dehydrated in an ethanol series, and embedded in paraffin according to standard methods. Sections (7 µm) were deparaffined, rehydrated, and treated for 15 minutes with a blotto blocking solution consisting of 5% non-fat dry milk powder in 10 mM PBS buffer. Subsequently, an anti-cellulase (Cel5) antibody in 2% blotto was layered on the sections after removing excess liquid. Incubation was performed in a high humidity incubator overnight at 4° C. Slides were then washed with PBS buffer containing 0.5% Tween 20, and 100 µl of FITC-conjugated anti-rabbit IgG (Sigma) was layered on the sections. Slides were incubated for 2 hours at room temperature, washed with PBS buffer and distilled water, and mounted with DABCO anti-fade solution. Images were captured with a Zeiss Axiophot microscope (Johnson et al., Gene Anal. Techniques 1:3-8, 1984). For confocal microscopy, sections were examined under a Zeiss LSM 310 microscope. A 488 nm argon laser and a 515-565 nm emission band-pass filter were used to visualize the FITC-conjugated antibody and a 543 nm HeNe laser line and a 590 nm emission high-pass filter were used to visualize the autofluorescence of chlorophyll.

Figure 2:
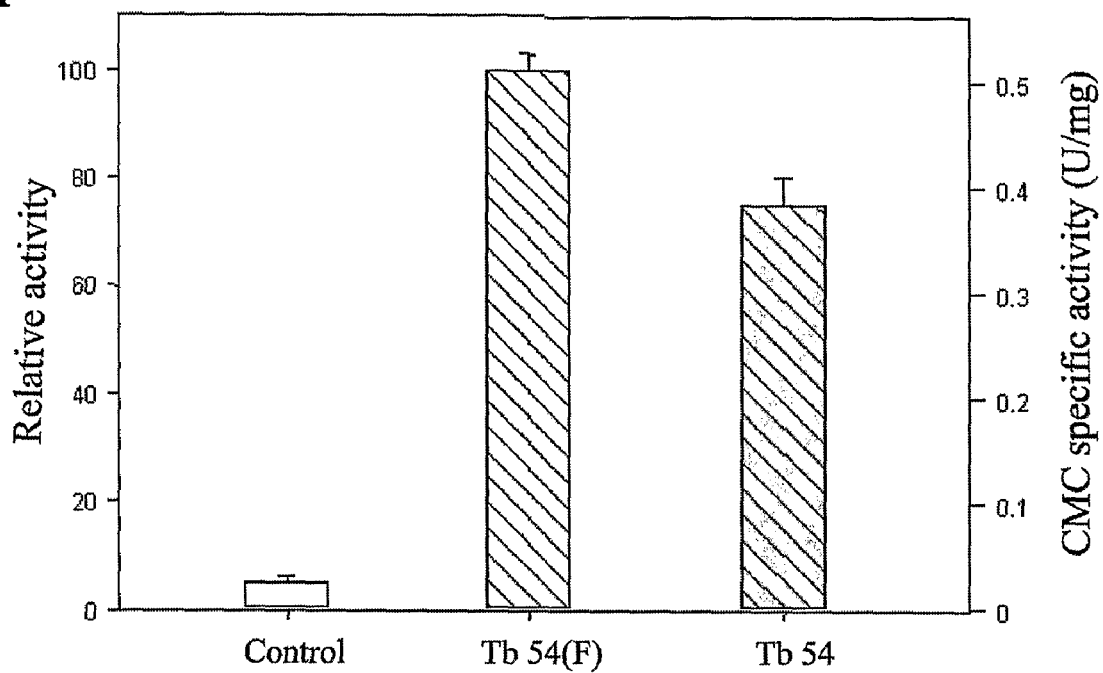
FIG. 2A is a graph showing the enzyme activities of protein extracts prepared from leaves of control plants transfected with basic vector, and transgenic plants Tb54(F) and Tb54 transfected with RbcS(tp):Cel5:CBM6 and Cel5:CBM6 recombinant genes, respectively.
FIG. 2B is a set of photographs showing the localization of a gene inserted into transgenic plants by treating cross sections of leaf fragments of transgenic plants with anti-cellulase (Cel5) antibody as the primary antibody and with FITC-conjugated anti-rabbit IgG as the secondary antibody (green) (the localization of chloroplast was confirmed by auto-fluorescent image of chlorophyll (red)),
  a: Transfected with basic vector
  b: Transfected with RbcS(tp):Cel5:CBM6
  c: Transfected with RbcS(tp):Cel5
Figure 2:
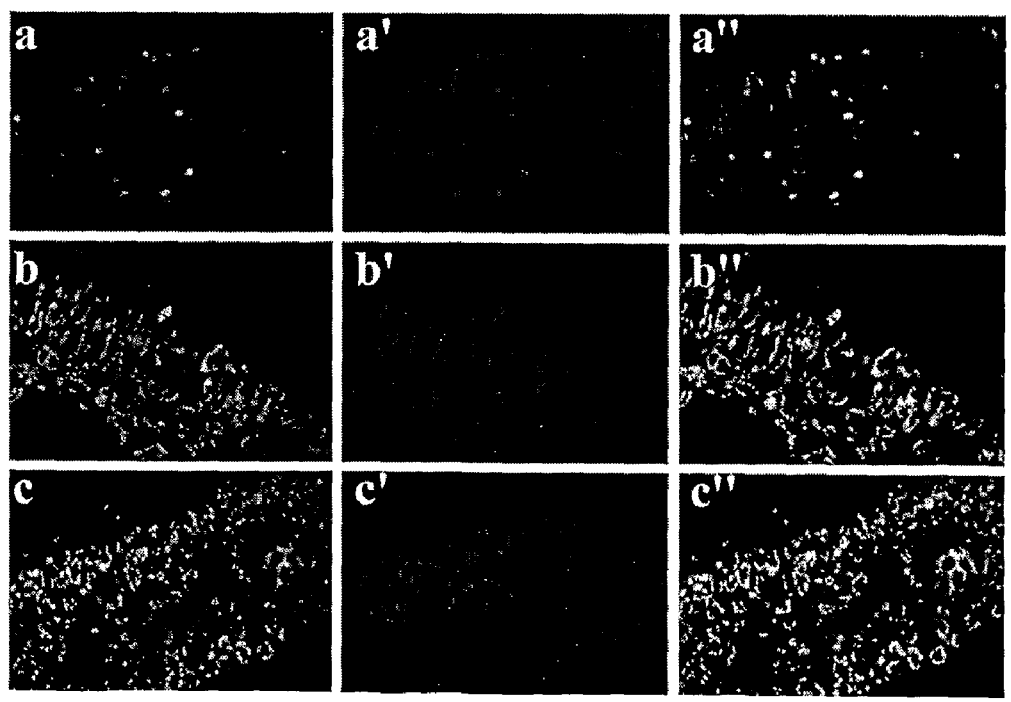

As a result, intense fluorescent signals were detected from the chloroplasts of leaf cells obtained from the transgenic plants, whereas the control non-transgenic plants did not show any significant signals (FIG. 2B).

<2-3> Cellulase Activity in a Transgenic Tobacco Plant

The cellulase activity expressed in transgenic tobacco plants were determined using carboxymethylcellulose (CMC) as a substrate from protein extracts obtained from fully grown up tobacco plant leaves. Particularly, the cellulase activity with CMC as the substrate was measured by the reduction in viscosity of 1% (w/c) CMC solution in 0.1 M phosphate buffer (pH 6.8) after 5 minute incubation with the sample at 37° C. One unit of enzyme activity was defined as the amount of enzyme required to reduce the viscosity of the CMC solution by one centipoise in 1 min.

As shown in FIG. 2A, total protein extracts of the transgenic plants showed strong cellulase activity compared to protein extracts obtained from transgenic plants harboring a vector without cellulase gene. Protein extracts obtained from transgenic plants expressing RbcS(tp):Cel5:CBM6 showed a slightly higher cellulase activity than those expressing RbcS(tp):Cel5.

EXAMPLE 3

Autohydrolysis Activity of Cellulose in a Transgenic Tobacco Plant

<3-1> Measurement of Autohydrolysis Activity of RbcS(tp):Cel5:CBM6 Expressed in a Transgenic Tobacco Plant The present inventors performed following experiments to examine whether the cellulase expressed in a transgenic tobacco plant could hydrolyze the cellulose of the cell wall after lysis of the cells.

Cel5:CBM6 expressed in *E. coli* was purified to be used to determine the activity, and the cellulase activity expressed in transgenic plants was determined without purification. To prepare crude extracts from the leaf tissues of transgenic tobacco plants, 1 g of leaf tissue was ground to homogeneity in 5 ml of protein extraction buffer (100 mM phosphate buffer, pH 6.8) with sea sand. The cellulase activity was determined using two different substrates, carboxymethylcellulose (CMC) and the insoluble cell wall components of plant stems. The cellulase activity with CMC as the substrate was measured with the same method as described in Example <2-3>, that is the cellulase activity was measured by the reduction in viscosity of an 1% (W/V) CMC solution in 0.1 M phosphate buffer (pH 6.8) after 5 minute incubation with the sample at 37° C. One unit of enzyme activity was defined as the amount of enzyme required to reduce the viscosity of the CMC solution by one centipoise in 1 min.

The cellulase activity with the cell wall components as the substrate was measured using 0.2 g of stems ground in liquid nitrogen and incubated in 5 ml of leaf extracts for 65 hours at 40° C. Samples were withdrawn at regular time intervals. The amount of reducing sugars released from the incubation mixture was determined by the DNS method using glucose as the standard (Miller, G. L. et al, Anal Biochem. 1:127-132, 1960).

Figure 3:
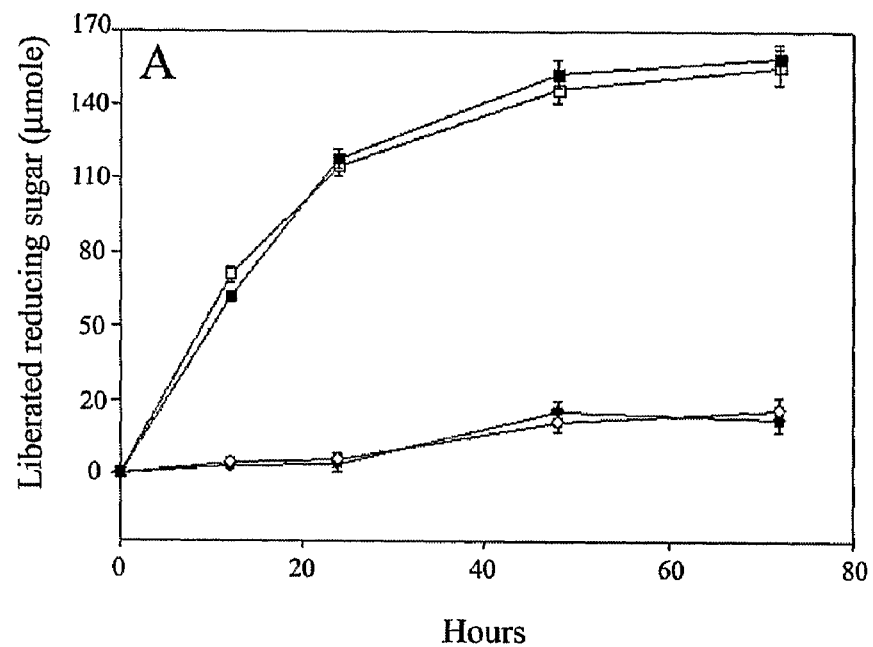
FIG. 3 is a set of graphs showing the results of investigation of autohydrolysis activity of RbcS(tp):Cel5:CBM6 cellulase. Cell extracts obtained from the transgenic tobacco leaves were reacted with cell wall fraction of tobacco stem alone (A) or together with the exogenous exoglucanase Cel6B (exo-beta-1,4 glucanase) (B), followed by quantification of sugar reducing ends by the DNS method,
  ●: Leaf extracts of transgenic plants harboring RbcS(tp):Cel5
  ○: Leaf extracts of transgenic plants harboring empty vector
  ■: Leaf extracts of transgenic plants harboring RbcS(tp):Cel5:CBM6
  □: Addition of Cel5:CBM6 expressed and purified from *E. coli*
  ▲: Exogenous Cel6B alone
  △: Leaf extracts of transgenic plants expressing RbcS(tp):Cel5:CBM6+ exogenous Cel6B
Figure 3:
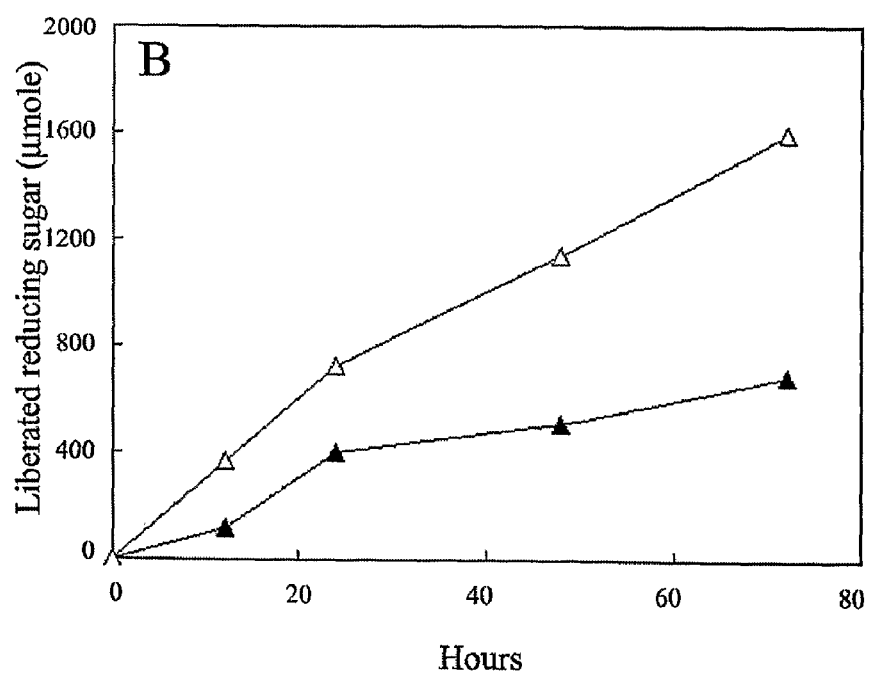

As a result, crude extracts of Tb54(F)-14 containing RbcS(tp):Cel5:CBM6 produced a large amount of soluble sugars from the insoluble cell wall fraction of the transgenic plants (FIG. 3A). Chemical analysis of the insoluble fraction obtained from the reaction mixture indicated that approximately 12% of the total insoluble cellulose components or the cell wall fraction was released as soluble sugars. In contrast, protein extracts obtained from Tb54-8 or non-transgenic plants showed negligible activity toward the cell wall fraction.

The present inventors compared the hydrolysis activity of RbcS(tp):Cel5:CBM6 with that of externally added Cel5:CBM6. As a result, when Cel5:CBM6 that was expressed and purified from *E. coli* was added to the cell wall fractions, the amount of soluble sugar released was nearly the same as that was obtained with equal amounts of RbcS(tp):Cel5:CBM6.

The amount of released soluble sugar may not accurately reflect the level of RbcS(tp):Cel5:CBM6 activity, because Cel5:CBM6 is an endoglucanase, which can only digest the cellulose internally. Soluble sugars are only released efficiently by the concerted action of an endoglucanase and exoglucanase. Therefore, the present inventors examined the efficiency of soluble sugar released by RbcS(tp):Cel5:CBM6 in the presence of an exogenously added exoglucanase. In the present invention, exoglucanase Cel6B, a β-1,4-glucan cellobiohydrolase, purified from *Thermobifidus fusca* was used.

As a result, when Cel6B was added to the autohydrolysis reaction mixture containing RbcS(tp):Cel5:CBM6, the amount of soluble sugar released was greatly increased compared to that released by the exoglucanase, Cel6B, alone. Chemical analysis of residual insoluble fraction revealed that approximately 40% of the total insoluble cellulose was released as soluble sugars. The above results indicate that RbcS(tp):Cel5:CBM6 may generate a large number of long polymeric oligosaccharides from cell walls that can be substrates for the exoglucanase.

<3-2> Analysis of Soluble Sugars Converted by RbcS(tp):Cel5:CBM6

The present inventors analyzed the released sugar compounds to better understand the mechanism of the autohydrolysis disclosed in the above Example <3-1>.

Particularly, protein extracts obtained from transgenic Tb54(F)-14 were incubated with the cell wall fractions for 72 hours, and sugar molecules were separated from the undigested materials by gel filtration. The liquid fraction was analyzed by HPLC (Millipore Waters 600E) using REZEX RSO oligosaccharides column (Phenomenex Inc.). Water at a flow rate of 0.3 ml/min was used as the elution solvent. Pure cellulo-oligosaccharides (1% w/v in 10 mM phosphate buffer (Seikagaku Corporation, Japan)) such as glucose (G1), cellobiose (G2), cellotriose (G3), cellotetraose (G4), cellopentaose (G5), and cellohexaose (G6) were used as standards.

Figure 4:
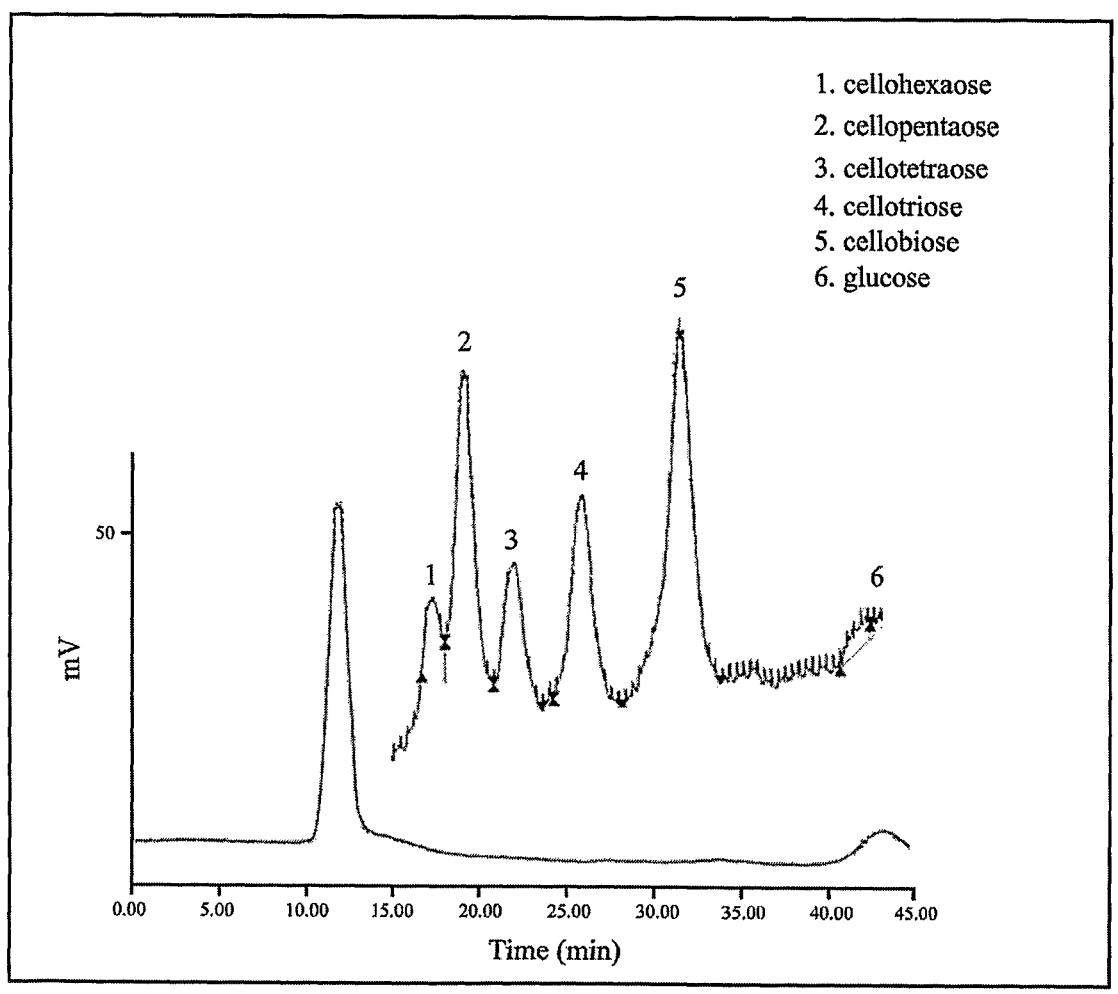
FIG. 4 is a graph showing the result of HPLC analysis of soluble sugars released by RbcS(tp):Cel5:CBM6. The cellulose components of cell walls were hydrolyzed by endogenously expressed RbcS(tp):Cel5:CBM6. After 72 hr incubation, soluble sugars were analyzed using a REZEX RSO oligosaccharide column.

As a result, as shown in FIG. 4, the breakdown products of autohydrolysis were mainly long polymeric oligosaccharides together with small amounts of glucose (FIG. 4).

This type of hydrolytic activity is expected since RbcS(tp):Cel5:CBM6 is an endoglucanase. The oligosaccharide chains were longer than cellohexaose, but the length of the oligosaccharide chain was reduced when the incubation time was increased.

The residual cell wall fraction obtained after autohydrolysis was also analyzed, using FTIR (Fourier Transform Infrared Spectroscopy). Particularly, IR spectra were taken with KBr pellets (1 mg of transgenic tobacco holocellulose in 300 mg KBr) using a Bio-Rad FTIR (FTS 175C) spectromet (Kacurakova et al., Carbohydr. Res. 337: 1145-1153, 2002). The plant cellulose content was determined with the alcohol-benzene extraction method (Goering, H. K. et al., Agriculture Handbook, 379, 1970).

As a result, from the comparison of spectra between the control and RbcS(tp):Cel5:CBM6-treated cell wall fractions was revealed that the major difference was decrease in the intensity of the bands assigned to the cellulose:glycosidic C—O—C bond of cellulose at 1157 $cm^{-1}$, the C—O—C bond at 1060 $cm^{-1}$, and the C—C bond at 898 $cm^{-1}$ in the RbcS(tp):Cel5:CBM6-treated cell wall fractions.

Figure 5:
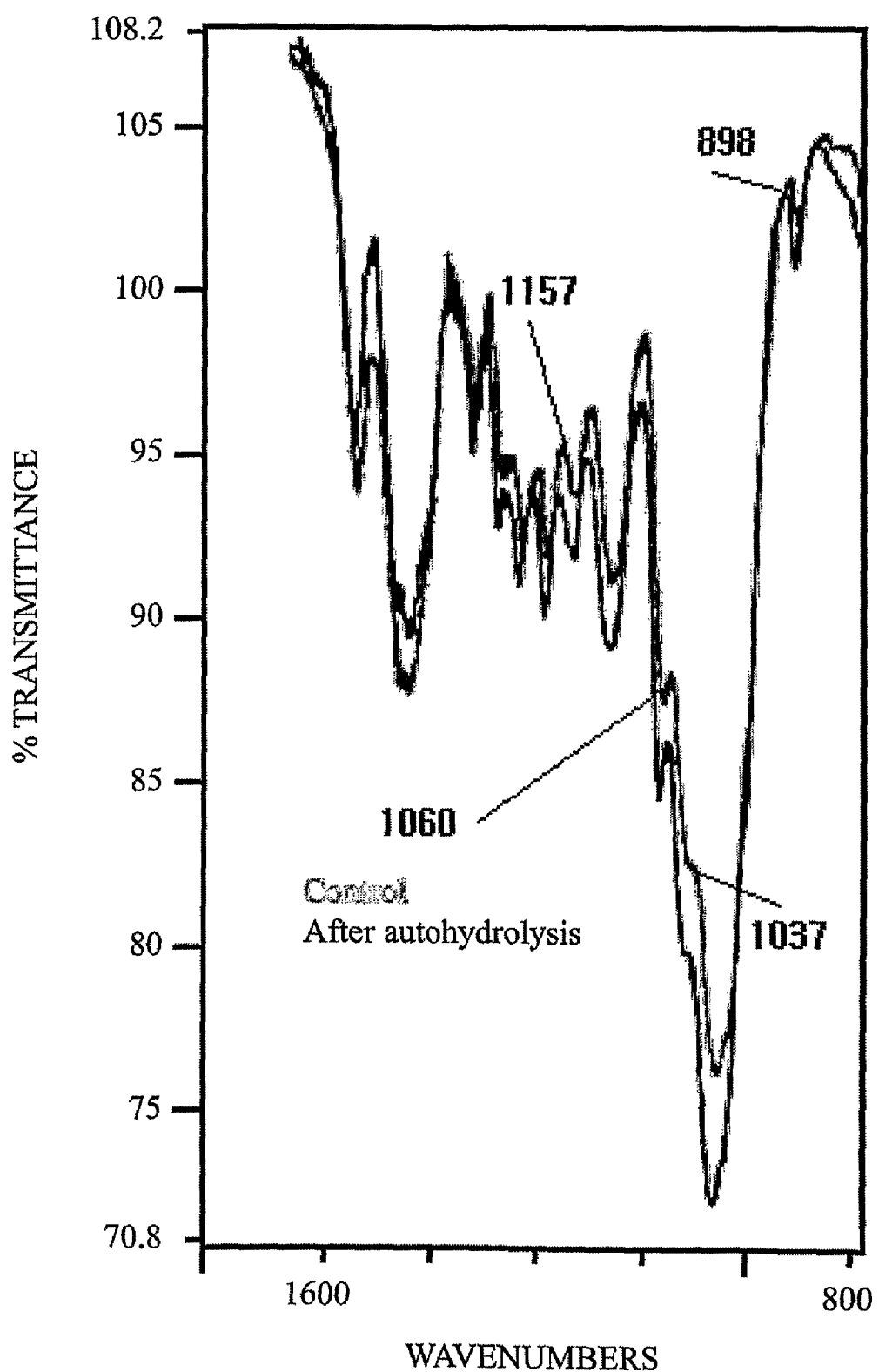
FIG. 5 is a graph showing the result of FTIR analysis of the residual material of the cell wall after autohydrolysis. The cellulose components of the cell walls were hydrolyzed with RbcS(tp):Cel5:CBM6, and analyzed with FTIR.

The above results proved that RbcS(tp):Cel5:CBM6 expressed in a transgenic plant of the invention has autohydrolysis activity in its own cell wall (FIG. 5).

INDUSTRIAL APPLICABILITY

As explained hereinbefore, a method of the present invention for production of a transgenic plant showing autohydrolysis activity against cellulose and production of soluble sugars using the same can enhance the production of soluble sugars from the cell wall materials of plant cells without the need for additional steps or an external source of enzymes. Thus, it is a highly cost-effective system for the production of soluble sugars, minimizing the enzyme production processes, compared with the conventional method using enzymes externally produced by fermentation on a large scale.

Sequence List Text

SEQ. ID. No 1 is the sequence of RbcS(tp):Cel5:CBM6, a recombinant cDNA harboring cellulase, cellulose binding domain and chloroplast targeting peptide.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An *Agrobacterium tumefaciens* LBA-4404 which is transformed with a plant expression vector harboring a recombinant cDNA represented by SEQ ID NO: 1, wherein *Agrobacterium tumefaciens* LBA-4404 is deposited at Korean Collection for Type Cultures under Accession No. KCTC 10834BP.

2. A method for the production of a transgenic plant expressing cellulase for autohydrolysis comprising the following steps:
   i) constructing a plant expression vector harboring a recombinant cDNA comprising a chloroplast-targeting peptide, a full length cellulase and a cellulose binding domain, wherein the chloroplast-targeting peptide is fused to N-terminus of the cellulase; and the cellulose binding domain is fused to the C-terminus of the cellulase;
   ii) transforming *Agrobacterium* with the expression vector obtained from step i);
   iii) inducing callus by introducing the transformed *Agrobacterium*, obtained from step ii), to a plant or plant cells; and
   iv) inducing plant growth by culturing the callus, obtained from step iii),
   wherein the transformed *Agrobacterium* of step ii) is *Agrobacterium tumefaciens* LBA-4404, which is deposited at Korean Collection for Type Cultures under Accession No. KCTC 10834BP.

3. A method for the production of soluble sugars comprising the following steps:
   i) obtaining homogenate from leaves or stems of a transgenic plant prepared by the method of claim 2;
   ii) incubating the homogenate obtained from step i) to induce autohydrolysis of cellulose; and
   iii) separating and purifying autohydrolyzed soluble sugars.

4. The method as set forth in claim 3, wherein an externally expressed and purified exoglucanase is added to the homogenate obtained from step i) before incubating in step ii).

* * * * *